US012573044B1

(12) United States Patent
Lu et al.

(10) Patent No.: US 12,573,044 B1
(45) Date of Patent: Mar. 10, 2026

(54) OPHTHALMIC MEDICAL IMAGE SEGMENTATION METHOD AND SYSTEM AND STORAGE MEDIUM

(71) Applicant: SUZHOU CITY UNIVERSITY, Suzhou (CN)

(72) Inventors: Xuemei Lu, Suzhou (CN); Zhihao Xu, Suzhou (CN); Qingquan Meng, Suzhou (CN); Lei Gao, Suzhou (CN)

(73) Assignee: SUZHOU CITY UNIVERSITY, Suzhou (CN)

( * ) Notice: Subject to any disclaimer, the term of this patent is extended or adjusted under 35 U.S.C. 154(b) by 0 days.

(21) Appl. No.: 19/214,033

(22) Filed: May 21, 2025

(30) Foreign Application Priority Data

Sep. 9, 2024 (CN) .......................... 202411254318.2

(51) Int. Cl.
G06T 7/00 (2017.01)
A61B 3/14 (2006.01)
G06T 7/11 (2017.01)
(52) U.S. Cl.
CPC .............. G06T 7/0012 (2013.01); A61B 3/14 (2013.01); G06T 7/11 (2017.01);
(Continued)
(58) Field of Classification Search
None
See application file for complete search history.

(56) References Cited

FOREIGN PATENT DOCUMENTS

| CN | 113343789 A | 9/2021 |
| CN | 118314350 A | 7/2024 |

OTHER PUBLICATIONS

Li, Xiang, et al. "Lightweight attention convolutional neural network for retinal vessel image segmentation." IEEE Transactions on Industrial Informatics 17.3 (2020): 1958-1967. (Year: 2020).*
(Continued)

*Primary Examiner* — Samah A Beg
(74) *Attorney, Agent, or Firm* — Zhu Lehnhoff LLP

(57) ABSTRACT

Ophthalmic medical image segmentation method includes dividing the medical image data into a training set and a test set according to an autonomously set proportion; constructing a convolutional neural network model adopting a U-shaped encoding and decoding structure based on an attention mechanism and a weighted loss function, and performing training; transmitting a to-be-segmented medical image to obtain a segmentation result, wherein the attention mechanism is introduced into the U-shaped encoding and decoding structure: a superficial layer feature map $I_{LE}$ of an encoder is subjected to convolution to obtain $I_{LE-1}$, and a deep layer feature map $I_{HD}$ of a decoder is subjected to up-sampling and convolution to obtain $I_{HD-1}$; the $I_{LE-1}$ and the $I_{HD-1}$ are multiplied to obtain $I_{Mul}$; the $I_{Mul}$ and the $I_{HD-1}$ are summed, and $I_{Sum}$ is then output through an activation function; and the $I_{Mul}$ and the $I_{Sum}$ are spliced, and then output to a target layer.

15 Claims, 4 Drawing Sheets

(52) U.S. Cl.
   CPC .............. *G06T 2207/10024* (2013.01); *G06T*
         *2207/10101* (2013.01); *G06T 2207/20081*
      (2013.01); *G06T 2207/20084* (2013.01); *G06T*
         *2207/30041* (2013.01); *G06T 2207/30096*
                                             (2013.01)

(56)                References Cited

OTHER PUBLICATIONS

Sambyal, Nitigya, et al. "Modified U-Net architecture for semantic segmentation of diabetic retinopathy images." Biocybernetics and Biomedical Engineering 40.3 (2020): 1094-1109. (Year: 2020).*
Sundar, Sumod, and S. Sumathy. "RetU-Net: An enhanced U-Net architecture for retinal lesion segmentation." International Journal on Artificial Intelligence Tools 32.04 (2023): 2350013. (Year: 2023).*
Tang, Shuyun, et al. "U-net with hierarchical bottleneck attention for landmark detection in fundus images of the degenerated retina." International Workshop on Ophthalmic Medical Image Analysis. Cham: Springer International Publishing, 2021. (Year: 2021).*
Tuyet, Vo Thi Hong, Nguyen Thanh Binh, and Dang Thanh Tin. "A Deep Bottleneck U-Net Combined with Saliency Map for Classifying Diabetic Retinopathy in Fundus Images." International Journal of Online & Biomedical Engineering 18.2 (2022). (Year: 2022).*
First official action in priority application No. CN2024112543182, issued on Oct. 12, 2024.
Notification of Grant of Invention Patent in priority application No. CN2024112543182, issued on Oct. 18, 2024.

* cited by examiner

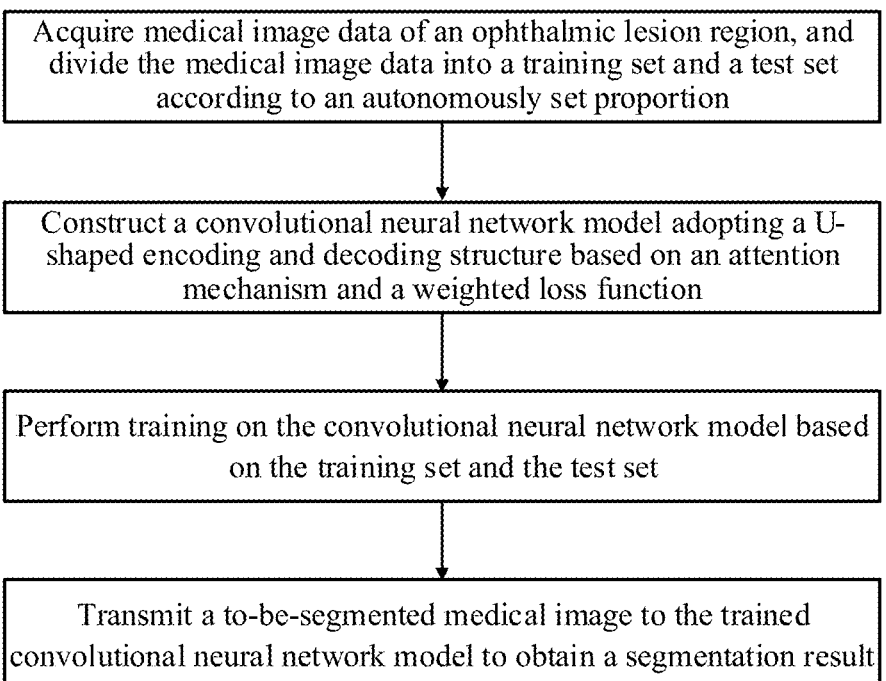

Acquire medical image data of an ophthalmic lesion region, and divide the medical image data into a training set and a test set according to an autonomously set proportion Construct a convolutional neural network model adopting a U-shaped encoding and decoding structure based on an attention mechanism and a weighted loss function Perform training on the convolutional neural network model based on the training set and the test set Transmit a to-be-segmented medical image to the trained convolutional neural network model to obtain a segmentation result

FIG.1

OPHTHALMIC MEDICAL IMAGE SEGMENTATION METHOD AND SYSTEM AND STORAGE MEDIUM

REFERENCE TO RELATED APPLICATIONS

The present application claims the priority of Chinese patent application No. 202411254318.2, filed on 2024 Sep. 9, the entire disclose of which is incorporated herein by reference.

TECHNICAL FIELD

The present invention relates to the technical field of medical image segmentation, in particular to an ophthalmic medical image segmentation method and system and a storage medium.

BACKGROUND

Medical image segmentation can make images of pathological structures clearer, and thus play an important role in computer-aided diagnosis and intelligent medical treatment.

The main difficulties in medical image segmentation for ophthalmic diseases are as follows: morphological features presented by a lesion region are diverse, with uneven size, shape and intensity distribution; and the boundary between the lesion region and surrounding tissues is unclear, possibly accompanied by complications of patients, such as effusion. These difficulties increase the complexity of medical image segmentation, and the results obtained by the existing ophthalmic medical image segmentation methods often contain a large number of relevant redundant information and irrelevant feature information, resulting in low segmentation progress and low efficiency.

In addition, the existing ophthalmic medical image segmentation methods use a single loss function to construct convolutional neural networks, which perform poorly when processing special samples, lack comprehensiveness, and have low segmentation accuracy.

SUMMARY OF THE INVENTION

For this purpose, the technical problem to be solved by the present invention is to overcome the problem that an ophthalmic medical image segmentation method in the prior art is low in segmentation efficiency and accuracy and lacks comprehensiveness, and to provide an ophthalmic medical image segmentation method and system and a storage medium, which achieve fast segmentation speed and high efficiency, and can obtain a high-accuracy segmentation result while possessing comprehensiveness.

In a first aspect, to solve the above technical problem, the present invention provides an ophthalmic medical image segmentation method. The method includes the following steps:

acquiring medical image data of an ophthalmic lesion region, and dividing the medical image data into a training set and a test set according to an autonomously set proportion;

constructing a convolutional neural network model adopting a U-shaped encoding and decoding structure based on an attention mechanism and a weighted loss function;

performing training on the convolutional neural network model based on the training set and the test set; and transmitting a to-be-segmented medical image to the trained convolutional neural network model to obtain a segmentation result, wherein the U-shaped encoding and decoding structure includes an encoder, a jump connection part, a bottleneck layer and a decoder; the bottleneck layer is located between the encoder and the decoder; the encoder is connected to the decoder through the jump connection part; and the attention mechanism is introduced into the U-shaped encoding and decoding structure:

a superficial layer feature map $I_{LE}$ of the encoder is subjected to a convolution operation to obtain $I_{LE\text{-}1}$, and a deep layer feature map $I_{HD}$ of the decoder is subjected to an up-sampling operation and the convolution operation to obtain $I_{HD\text{-}1}$: the $I_{LE\text{-}1}$ and the $I_{HD\text{-}1}$ are multiplied to obtain $I_{Mul}$; the $I_{Mul}$ and the $I_{HD\text{-}1}$ are summed, and $I_{Sum}$ is then output through an activation function; and the $I_{Mul}$ and the $I_{Sum}$ are spliced, and then output to a target layer.

In one embodiment of the present invention, a method of splicing the $I_{Mul}$ and the $I_{Sum}$ is as follows:

$$I_{Mul} = I_{HD-1} \otimes I_{LE-1};$$

$$I_{Sum} = ReLU(I_{Mul} \oplus I_{HD-1});$$

$$I_{Att} = Concat[I_{Sum}, I_{HD-1}];$$

wherein $\otimes$ represents that the feature maps are multiplied by pixels, $\oplus$ represents that the feature maps are summed by pixels, ReLU represents the activation function, Concat represents a splicing function, and $I_{Att}$ represents output after splicing.

In one embodiment of the present invention, the weighted loss function is constructed using a multi-loss fusion method, which is as follows:

a multi-classified logistic loss function, a Dice loss function and a binary cross entropy loss function are fused to obtain the weighted loss function $$\text{Loss}_{All} : \text{Loss}_{All} = \lambda_1 L_{logistic}(Y, \hat{Y}) + \lambda_2 L_{Dice}(Y, \hat{Y}) + \lambda_3 L_{BCE}(Y, \hat{Y});$$

wherein $\lambda_1$ is a weight of the multi-classified logistic loss function; $L_{logistic}(Y,\hat{Y})$ represents the multi-classified logistic loss function; $\lambda_2$ represents a weight of the Dice loss function; $L_{Dice}(Y,\hat{I})$ represents the Dice loss function; $\lambda_3$ represents a weight of the binary cross entropy loss function; $L_{BCE}(Y,\hat{Y})$ represents the binary cross entropy loss function; $\lambda_1,\lambda_2,\lambda_3$ are all real numbers, and $\lambda_1+\lambda_2+\lambda_3=1$; and initial values of $\lambda_1,\lambda_2,\lambda_3$ are 0.4, 0.4, and 0.2 respectively.

In one embodiment of the present invention, the multi-classified logistic loss function $L_{logistic}(Y,\hat{Y})$ is as follows:

$$L_{logistic}(Y, \hat{Y}) = -\sum_{\substack{x_i \in \Omega \\ i=1}}^{N} \omega_{logloss}(x_i) \cdot Y(x_i) \cdot \log[\hat{Y}(x_i)];$$

$$\omega_{logloss}(x_i) = \begin{cases} 10, x_i \in ROI \\ 1, x_i \in BACKGROUND \end{cases};$$

wherein N is the number of pixel points, $x_i$ represents the $i^{th}$ pixel point, $\Omega$ represents a category of classification, $\Sigma$ is a summing symbol, $Y(x_i)$ represents a network segmentation result of the $i^{th}$ pixel point $x_i$, log represents that a logarithm is taken, $\hat{Y}(x_i)$ represents an expected segmentation result of the $i^{th}$ pixel point $x_i$, ROI represents a lesion region of interest, and BACK-GROUND represents a background region;

the Dice loss function $L_{Dice}(Y, \hat{Y})$ is as follows:

$$L_{Dice}(Y, \hat{Y}) = 1 - \frac{2 \cdot [Y(x_i) \odot \hat{Y}(x_i)]}{\sum_{i=1}^{N} |Y(x_i)| + \sum_{i=1}^{N} |\hat{Y}(x_i)|};$$

wherein $\odot$ represents that the corresponding pixels are multiplied, and $\|$ represents that an absolute value is taken; and the binary cross entropy loss function $L_{BCE}(Y, \hat{Y})$ is as follows:

$$L_{BCE}(Y, \hat{Y}) = -\frac{1}{N} \sum_{i=1}^{N} \{Y(x_i) \log[\hat{Y}(x_i)]\} + [1 - Y(x_i)] \cdot \log[1 - \hat{Y}(x_i)].$$

In one embodiment of the present invention, the encoder is configured with a plurality of layers, and each layer is subjected to the convolution operation, a batch normalization operation and a maximum pooling operation; and the size of a convolution kernel and the number of operations for each layer to perform the convolution operation can be set autonomously.

In one embodiment of the present invention, the encoder is configured with four layers, each layer is subjected to the convolution operation twice based on a convolution layer having a convolution kernel size of 3*3 and a step size of 1, and each layer is subjected to the maximum pooling operation based on a pooling layer having a pooling kernel size of 2*2.

In one embodiment of the present invention, the medical image data includes OCT image data of ophthalmic choroidal neovascularization and fundus color image data of glaucoma, and the OCT image data and the fundus color image data both contain original image data and corresponding gold standard image data.

In one embodiment of the present invention, background pixel values in the OCT image data and the fundus color image data are assigned to 0, and the same pixel values are assigned to the lesion regions of the respective categories in the corresponding gold standard image data and incremented sequentially according to their categories.

In a second aspect, to solve the above technical problem, the present invention further provides an ophthalmic medical image segmentation system. The system includes:

a data acquisition module, configured to acquire medical image data of an ophthalmic lesion region, and divide the medical image data into a training set and a test set according to an autonomously set proportion;

a model construction module, configured to construct a weighted loss function by using a multi-loss fusion manner and construct a convolutional neural network model adopting a U-shaped encoding and decoding structure based on an attention mechanism and the weighted loss function;

a model training module, configured to perform training on the convolutional neural network model based on the training set and the test set; and an image segmentation module, configured to transmit a to-be-segmented medical image to the trained convolutional neural network model to obtain a segmentation result, wherein the U-shaped encoding and decoding structure includes an encoder, a bottleneck layer, a decoder and a jump connection part; the bottleneck layer is located between the encoder and the decoder; the attention mechanism is introduced into the decoder and the jump connection part:

a superficial layer feature map $I_{LE}$ of the encoder is subjected to a convolution operation to obtain $I_{LE-1}$, and a deep layer feature map $I_{HD}$ of the decoder is subjected to an up-sampling operation and the convolution operation to obtain $I_{HD-1}$; the $I_{LE-1}$ and the $I_{HD-1}$ are multiplied to obtain $I_{Mul}$; the $I_{Mul}$ and the $I_{HD-1}$ are summed, and $I_{Sum}$ is then output through an activation function; and the $I_{Mul}$ and the $I_{Sum}$ are spliced, and then output to a target layer.

In a third aspect, to solve the above technical problem, the present invention further provides a computer-readable storage medium having stored a computer program therein, the computer program, when executed by a processor, implementing the steps of the ophthalmic medical image segmentation method.

Compared with the prior art, the above technical solutions of the present invention have the following beneficial effects.

According to the ophthalmic medical image segmentation method and system and the storage medium provided by the present invention, the convolutional neural network model adopting the U-shaped encoding and decoding structure is constructed based on the attention mechanism and the weighted loss function, such that the segmentation progress of medical images is fast and efficient; special samples can be effectively processed, achieving comprehensiveness; and the segmentation results are highly accurate.

BRIEF DESCRIPTION OF THE DRAWINGS

In order to make the content of the present invention more clearly understandable, the present invention will be further described in detail below in conjunction with specific embodiments and accompanying drawings.

FIG. 1 is a flowchart of steps of an ophthalmic medical image segmentation method in a preferred embodiment of the present invention;

DETAILED DESCRIPTION OF THE PREFERRED EMBODIMENTS

Figure 2:
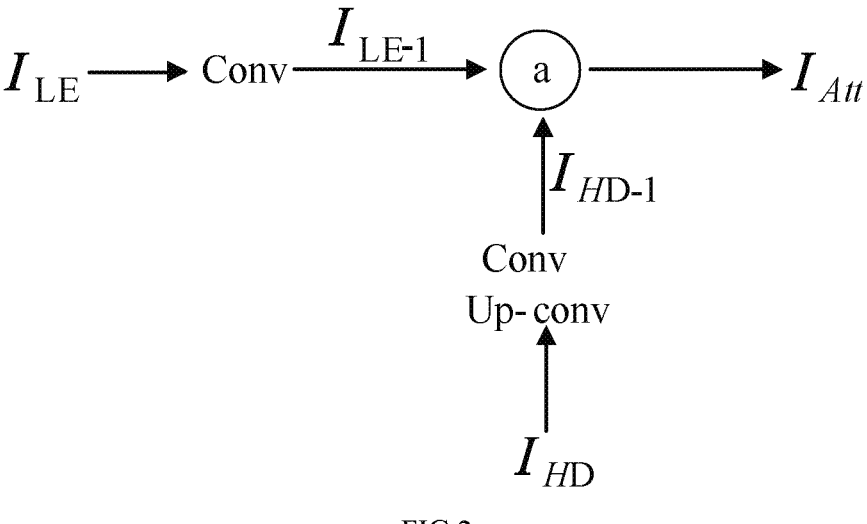
FIG. 2 is a schematic diagram of an attention module in a preferred embodiment of the present invention.

It is to be understood that the specific embodiments described herein are only used for explaining the present application, and are not used for limiting the present application.

The technical solutions in the embodiments of the present application will be described clearly and completely below in conjunction with accompanying drawings in the embodiments of the present application. Of course, the described embodiments are merely some embodiments, rather than all embodiments, of the present application.

Medical image segmentation for ophthalmic diseases needs to be achieved in combination with disease characteristics. For example, choroidal neovascularization (CNV) is a typical symptom of age-related macular degeneration. The rupture of the neovascularization of a choroidal layer in a retinal layer will cause decreased vision or even blindness in patients. Glaucoma is characterized by an increase in areas of an optic cup and an optic disc. In addition, optical coherence tomography (OCT) is a high-resolution non-invasive imaging technology that may record and display various structures of the fundus.

Efficient and accurate medical image segmentation of OCT images accompanied by CNV and glaucoma fundus color images is exactly the invention objective that the inventors of embodiments of the present application intend to achieve. Therefore, the embodiments of the present application provide an ophthalmic medical image segmentation method and system and a storage medium.

Embodiment 1

The present embodiment provides an ophthalmic medical image segmentation method. As shown in FIG. 1, the method includes the following steps:

acquiring medical image data of an ophthalmic lesion region, and dividing the medical image data into a training set and a test set according to an autonomously set proportion; constructing a convolutional neural network model adopting a U-shaped encoding and decoding structure based on an attention mechanism and a weighted loss function;

performing training on the convolutional neural network model based on the training set and the test set; and transmitting a to-be-segmented medical image to the trained convolutional neural network model to obtain a segmentation result, wherein the U-shaped encoding and decoding structure includes an encoder, a jump connection part, a bottleneck layer and a decoder; the bottleneck layer is located between the encoder and the decoder; the encoder is connected to the decoder through the jump connection part; and the attention mechanism is introduced into the U-shaped encoding and decoding structure:

a superficial layer feature map $I_{LE}$ of the encoder is subjected to a convolution operation to obtain $I_{LE-1}$, and a deep layer feature map $I_{HD}$ of the decoder is subjected to an up-sampling operation and the convolution operation to obtain $I_{HD-1}$; the $I_{LE-1}$ and the $I_{HD-1}$ are multiplied to obtain $I_{Mul}$; the $I_{Mul}$ and the $I_{HD-1}$ are summed, and $I_{Sum}$ is then output through an activation function; and the $I_{Mul}$ and the $I_{Sum}$ are spliced, and then output to a target layer.

According to the ophthalmic medical image segmentation method provided by the present embodiment, the convolutional neural network model adopting the U-shaped encoding and decoding structure is constructed, the attention mechanism is introduced in the U-shaped encoding and encoding structure, and the convolutional neural network model adopts the weighted loss function, such that (1) the segmentation progress of medical images is fast and efficient; (2) special samples can be effectively processed, achieving comprehensiveness; and (3) the segmentation results of the medical images are highly accurate.

Next, the ophthalmic medical image segmentation method provided by the present embodiment will be described in detail.

I. Principle of Method

Step 1:

specifically, acquiring medical image data of an ophthalmic lesion region, and dividing the medical image data into a training set and a test set according to an autonomously set proportion.

Optionally, medical images of the ophthalmic lesion region are labeled, the medical image data is acquired, and the medical image data is divided into a training set and a test set according to a proportion of 8:2.

Optionally, the medical image data includes OCT image data of ophthalmic choroidal neovascularization and fundus color image data of glaucoma, and the OCT image data and the fundus color image data both contain original image data and corresponding gold standard image data, wherein the gold standard image represents segmented regions manually labeled by a professional doctor or under the guidance of a professional doctor.

Optionally, background pixel values in the OCT image data and the fundus color image data are assigned to 0, and the same pixel values are assigned to the lesion regions of the respective categories in the corresponding gold standard image data and incremented sequentially according to their categories.

Step 2:

specifically, constructing a convolutional neural network model adopting a U-shaped encoding and decoding structure based on an attention mechanism and a weighted loss function;

Specifically, the U-shaped encoding and decoding structure includes an encoder, a jump connection part, a bottleneck layer and a decoder; the bottleneck layer is located between the encoder and the decoder; the encoder is connected to the decoder through the jump connection part; and as shown in FIG. 2, the attention mechanism is introduced into the U-shaped encoding and decoding structure to obtain an attention module:

a superficial layer feature map $I_{LE}$ of the encoder is subjected to a convolution operation Conv to obtain $I_{LE-1}$, and a deep layer feature map $I_{HD}$ of the decoder is subjected to an up-sampling operation Up-conv and the convolution operation Conv to obtain $I_{HD-1}$; the $I_{LE-1}$ and the $I_{HD-1}$ are multiplied to obtain $I_{Mul}$; the $I_{Mul}$ and the $I_{HD-1}$ are summed, and $I_{Sum}$ is then output through an activation function; and the $I_{Mul}$ and the $I_{Sum}$ are spliced, and then output to a target layer.

Optionally, a method of splicing the $I_{Mul}$ and the $I_{Sum}$ is as follows:

$$I_{Mul} = I_{HD-1} \otimes I_{LE-1};$$

$$I_{Sum} = ReLU(I_{Mul} \oplus I_{HD-1});$$

$$I_{Att} = Concat[I_{Sum}, I_{HD-1}];$$

wherein $\otimes$ represents that the feature maps are multiplied by pixels, $\oplus$ represents that the feature maps are summed by pixels, ReLU represents the activation function, Concat represents a splicing function, and $I_{Att}$ represents output after splicing.

Specifically, the encoder is configured with a plurality of layers, and each layer is subjected to the convolution operation, a batch normalization operation and a maximum pooling operation; and the size of a convolution kernel and the number of operations for each layer to perform the convolution operation can be set autonomously.

Specifically, the increase in the number of layers of the encoder can capture more feature levels, but will increase the computational cost and memory requirements and increase the training difficulty; the decrease in the number of layers of the encoder will usually make a constructed network model simpler and reduce the amount of computation, but also reduce the expressive ability of the constructed network model, making it difficult to capture detailed features.

Preferably, the encoder is configured with four layers, each layer is subjected to the convolution operation twice based on a convolution layer having a convolution kernel size of 3*3 and a step size of 1, and each layer is subjected to the maximum pooling operation based on a pooling layer having a pooling kernel size of 2*2.

Figure 3:
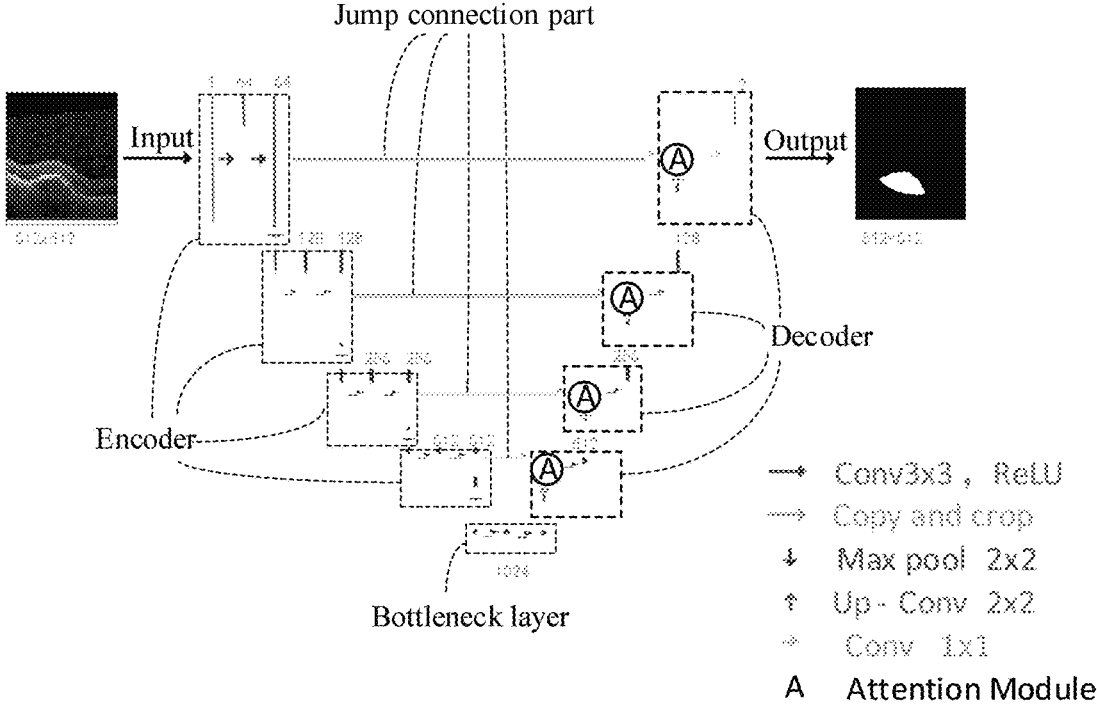
FIG. 3 is a schematic diagram of a U-shaped encoding and decoding structure by taking an OCT image of 512× 512CNV as an example in a preferred embodiment of the present invention.

Exemplarily, as shown in FIG. 3, by taking an OCT image of 512×512CNV as an example, this image is input into the left encoder section, and each layer of the encoder performs the convolution operation twice, and then performs the maximum pooling operation to reduce a spatial resolution; the number of channels of a convolutional feature map gradually increases from 64 at the beginning to 128, 256, 512 and 1024 sequentially after passing through the encoder layer by layer; and the right decoder section corresponds to the left encoder section, deep layer features in each layer of the decoder are subjected to the up-sampling operation and then integrated together with low layer features of the corresponding encoder section into the attention module A, and the number of channels of the convolutional feature map is adjusted sequentially to 512, 256, 128, and 2.

In FIG. 3, Conv3×3 represents that the convolution operation is performed based on a convolution layer having a convolution kernel size of 3*3; ReLU represents the activation function; Copy and crop represents that the splicing operation is performed; Max pool2×2 represents that the maximum pooling operation is performed based on a pooling layer having a pooling kernel size of 2*2; Up-Conv2×2 represents that the up-sampling operation of 2*2 is performed; and Attention Module represents the attention module A.

Specifically, in the above example, rich information of the superficial layer features of the encoder is transmitted to a deep network, thereby improving the overall performance of the convolutional neural network model.

Specifically, the U-shaped encoding and decoding structure can effectively focus the lesion region, suppress interference caused by other irrelevant regions, and improve the segmentation accuracy of the lesion region.

Specifically, the weighted loss function is constructed using a multi-loss fusion method, which is as follows:

a multi-classified logistic loss function, a Dice loss function and a binary cross entropy loss function are fused to obtain the weighted loss function $$Loss_{All} : Loss_{All} = \lambda_1 L_{logistic}(Y, \hat{Y}) + \lambda_2 L_{Dice}(Y, \hat{Y}) + \lambda_3 L_{BCE}(Y, \hat{Y});$$

wherein $\lambda_1$ is a weight of the multi-classified logistic loss function; $L_{logistic}(Y,\hat{Y})$ represents the multi-classified logistic loss function; represents a weight of the Dice loss function; $L_{Dice}(Y,\hat{Y})$ represents the Dice loss function; $\lambda_3$ represents a weight of the binary cross entropy loss function; $L_{BCE}(Y,\hat{Y})$ represents the binary cross entropy loss function; $\lambda_1, \lambda_2, \lambda_3$ are all real numbers, and $\lambda_1 + \lambda_2 + \lambda_3 = 1$; and initial values of $\lambda_1, \lambda_2, \lambda_3$ are 0.4, 0.4, and 0.2 respectively.

Specifically, the multi-classified logistic loss function $L_{logistic}(Y,\hat{Y})$ is as follows:

$$L_{logistic}(Y, \hat{Y}) = -\sum_{\substack{x_i \in \Omega \\ i=1}}^{N} \omega_{logloss}(x_i) \cdot Y(x_i) \cdot \log[\hat{Y}(x_i)];$$

$$\omega_{logloss}(x_i) = \begin{cases} 10, x_i \in ROI \\ 1, x_i \in BACKGROUND \end{cases};$$

wherein N is the number of pixel points, $x_i$ represents the $i^{th}$ pixel point, $\Omega$ represents a category of classification, $\Sigma$ is a summing symbol, $Y(x_i)$ represents a network segmentation result of the $i^{th}$ pixel point $x_i$, log represents that a logarithm is taken, $\hat{Y}(x_i)$ represents an expected segmentation result of the $i^{th}$ pixel point $x_i$, ROI represents a lesion region of interest, and BACKGROUND represents a background region.

Specifically, in the multi-classified logistic loss function $L_{logistic}(Y,\hat{Y})$, the weight of 1 the background region BACKGROUND is set to 1 by setting the weight of the lesion region of interest ROI to 10, such that the segmentation accuracy is enhanced in such a way that a high weight is given to the lesion region of interest ROI.

Specifically, the Dice loss function $L_{Dice}(Y,\hat{Y})$ is as follows:

$$L_{Dice}(Y, \hat{Y}) = 1 - \frac{2 \cdot [Y(x_i) \odot \hat{Y}(x_i)]}{\sum_{i=1}^{N} |Y(x_i)| + \sum_{i=1}^{N} |\hat{Y}(x_i)|};$$

wherein $\odot$ represents that the corresponding pixels are multiplied, and $\|$ represents that an absolute value is taken.

Specifically, the binary cross entropy loss function $L_{BCE}$ (Y,Ŷ) is as follows:

$$L_{BCE}(Y, \hat{Y}) = -\frac{1}{N}\sum_{i=1}^{N}\{Y(x_i)\log[\hat{Y}(x_i)]\} + [1 - Y(x_i)] \cdot \log[1 - \hat{Y}(x_i)].$$

Specifically, parameters in the convolutional neural network model are learned and updated based on the weighted loss function to balance the effectiveness between various indicators, and to improve the generalization ability of the convolutional neural network model; to reduce the phenomena of missing segmentation and over-segmentation; and to ensure the accuracy and consistency of the segmentation results.

Step 3:
specifically, performing training on the convolutional neural network model based on the training set and the test set.

Step 4:
specifically, transmitting a to-be-segmented medical image to the trained convolutional neural network model to obtain a segmentation result.

II. Data Validation

Exemplarily, OCT image data accompanied by CNV from a hospital is collected, in which an original image has a size of 1300×800, the training set has a size of 1200, and the test set has a size of 300. In order to reduce the training time and memory usage, a down-sampling operation is performed, and the size of the original image is compressed to 512×512.

Exemplarily, glaucoma fundus color image data from a public data set Drishti-GS is collected, in which an original image has a size of 512×512, the training set has a size of 80, and the test set has a size of 20.

Specifically, in order to quantitatively evaluate the segmentation performances of an ophthalmic medical image segmentation method provided by the present embodiment, evaluation indicators shown in Table 1 are used.

TABLE 1

| Evaluation indicators | Definition | Annotations |
|---|---|---|
| Dice coefficient | $Dice = \frac{2 \times (B \cap C)}{(\lvert B \rvert + \lvert C \rvert)}$ | B represents an algorithm segmentation result C represents a standard segmentation result |
| Recall rate | $Recall = \frac{TP}{TP + FN}$ | TP represents true positive FN represents false negative |

10

TABLE 1-continued

| Evaluation indicators | Definition | Annotations |
|---|---|---|
| Accuracy | $Accuracy = \frac{TP + TN}{TS}$ | TN represents true negative TS represents the total number of all samples |

Specifically, the convolutional neural network model described in the present embodiment is trained and tested based on a public platform PyTorch, and a stochastic gradient descent algorithm is used to optimize the parameters; and the batch size of an input image is set to 8, the learning rate is set to 8*10-4, the number of training rounds is set to 200, and the batch size of a validated image is set to 2.

Figure 4:
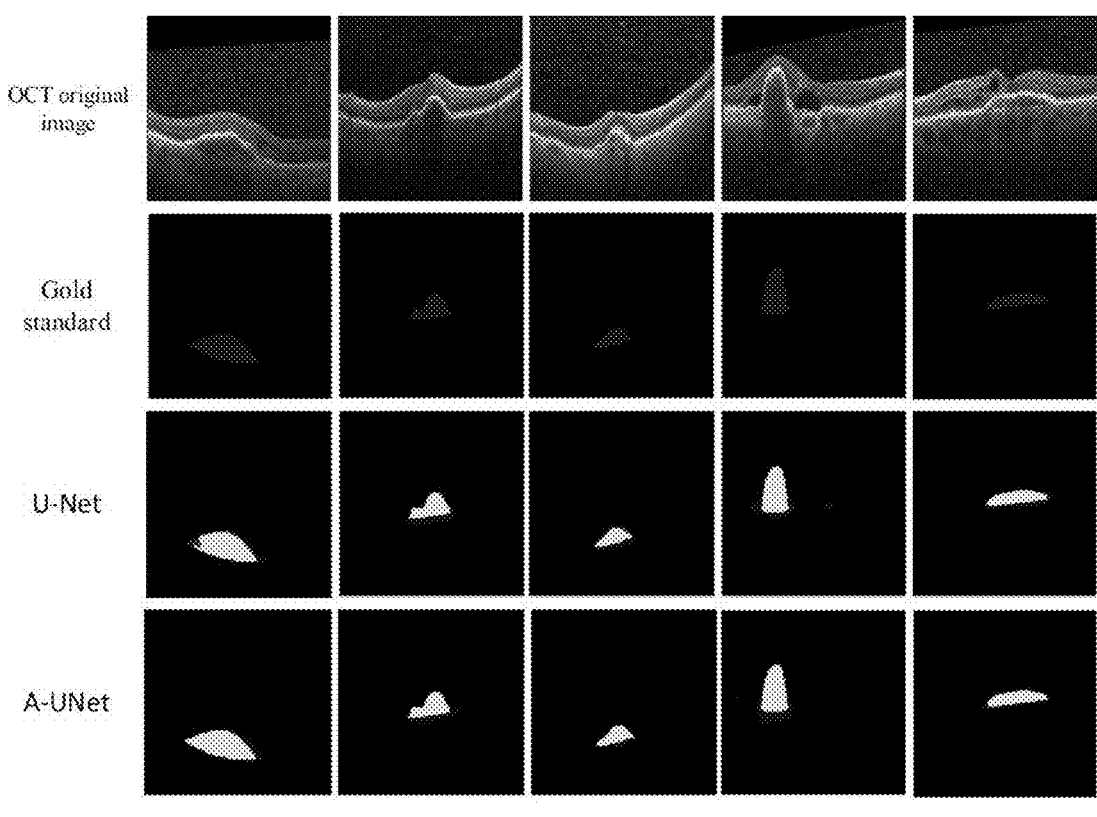
FIG. 4 is a visual comparison diagram of segmentation performances of U-Net and A-UNet on an OCT test diagram accompanied by CNV in a preferred embodiment of the present invention.

Specifically, Table 2 shows the comparison of segmentation performances of U-Net and A-UNet on an OCT test diagram accompanied by CNV; and FIG. 4 shows the visual comparison of segmentation performances of U-Net and A-UNet on the OCT test diagram accompanied by CNV, where green represents a segmentation result, white represents missing segmentation, and blue represents over-segmentation.

TABLE 2

| Unit: pixel points | | Test diagram 1 | Test diagram 2 | Test diagram 3 | Test diagram 4 | Test diagram 5 |
|---|---|---|---|---|---|---|
| Gold standard | | 9688 | 4727 | 3433 | 7337 | 4734 |
| U-Net | Missing segmentation | 958 | 157 | 614 | 90 | 0 |
| | Segmentation result | 8730 | 4570 | 2819 | 7247 | 4734 |
| | Over-segmentation | 2649 | 3154 | 1395 | 4229 | 2851 |
| A-UNet | Missing segmentation | 19 | 63 | 359 | 1 | 0 |
| | Segmentation result | 9669 | 4664 | 3074 | 7336 | 4734 |
| | Over-segmentation | 2014 | 2268 | 793 | 3432 | 1635 |

U-Net represents the existing convolutional neural network model, and A-UNet represents the convolutional neural network model described in the present embodiment.

Specifically, Table 3 shows the comparison of segmentation performances of U-Net and A-UNet at different learning rates.

TABLE 3

| Network | Learning rate | 1e–4 | 2e–4 | 3e–4 | 4e–4 | 5e–4 |
|---|---|---|---|---|---|---|
| U-Net | Dice | 0.354 | 0.389 | 0.407 | 0.397 | 0.426 |
| | Recall/% | 71.22 | 71.85 | 71.88 | 72.03 | 72.46 |
| | Accuracy/% | 70.14 | 70.42 | 70.76 | 71.38 | 71.68 |
| Network | Learning rate | 6e–4 | 7e–4 | 8e–4 | 9e–4 | 10e–4 |
| U-Net | Dice | 0.422 | 0.506 | 0.572 | 0.536 | 0.468 |
| | Recall/% | 73.32 | 74.66 | 73.68 | 72.47 | 72.89 |
| | Accuracy/% | 72.58 | 73.64 | 74.48 | 72.78 | 72.68 |
| Network | Learning rate | 1e–4 | 2e–4 | 3e–4 | 4e–4 | 5e–4 |
| A-UNet | Dice | 0.515 | 0.545 | 0.586 | 0.624 | 0.638 |
| | Recall/% | 76.22 | 76.43 | 77.24 | 77.56 | 78.64 |
| | Accuracy/% | 76.32 | 76.39 | 78.64 | 77.58 | 78.39 |

TABLE 3-continued

| Network | Learning rate | 6e–4 | 7e–4 | 8e–4 | 9e–4 | 10e–4 |
|---|---|---|---|---|---|---|
| A-UNet | Dice | 0.645 | 0.687 | 0.742 | 0.677 | 0.624 |
|  | Recall/% | 78.54 | 79.20 | 79.84 | 80.14 | 78.64 |
|  | Accuracy/% | 78.88 | 79.64 | 81.28 | 80.43 | 79.52 |

Figure 5:
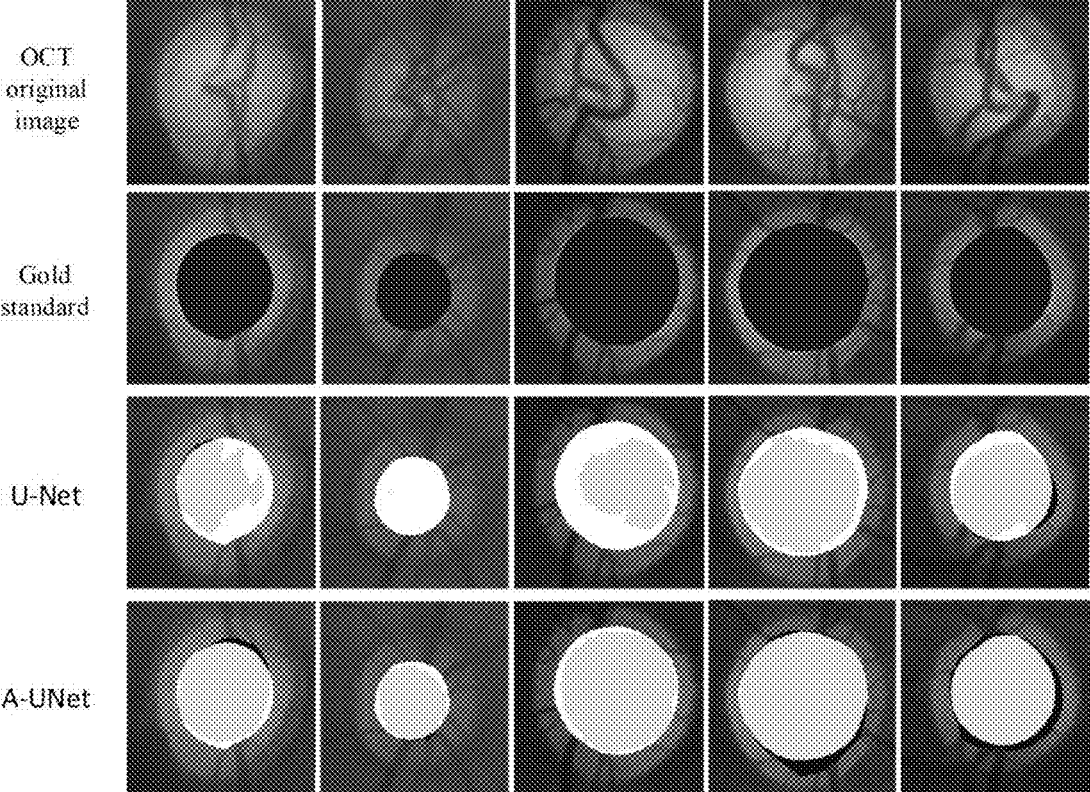
FIG. 5 is a visual comparison diagram of optic cup segmentation performances of U-Net and A-UNet on a glaucoma fundus color test diagram in a preferred embodiment of the present invention.

Specifically, Table 4 shows the comparison of optic cup segmentation performances of U-Net and A-UNet on a glaucoma fundus color test diagram; and FIG. 5 shows the visual comparison of optic cup segmentation performances of U-Net and A-UNet on the glaucoma fundus color test diagram.

TABLE 4

| Unit: pixel points |  | Test diagram 1 | Test diagram 2 | Test diagram 3 | Test diagram 4 | Test diagram 5 |
|---|---|---|---|---|---|---|
| Gold standard |  | 57314 | 33445 | 90010 | 93838 | 62449 |
| U-Net | Missing segmentation | 21712 | 33377 | 47164 | 19021 | 10795 |
|  | Segmentation result | 35602 | 68 | 42846 | 74817 | 51654 |
|  | Over-segmentation | 644 | 0 | 0 | 0 | 2424 |
| A-UNet | Missing segmentation | 4799 | 4877 | 10995 | 594 | 3 |
|  | Segmentation result | 52515 | 28568 | 79015 | 93244 | 62446 |
|  | Over-segmentation | 2145 | 513 | 0 | 9270 | 12037 |

Figure 6:
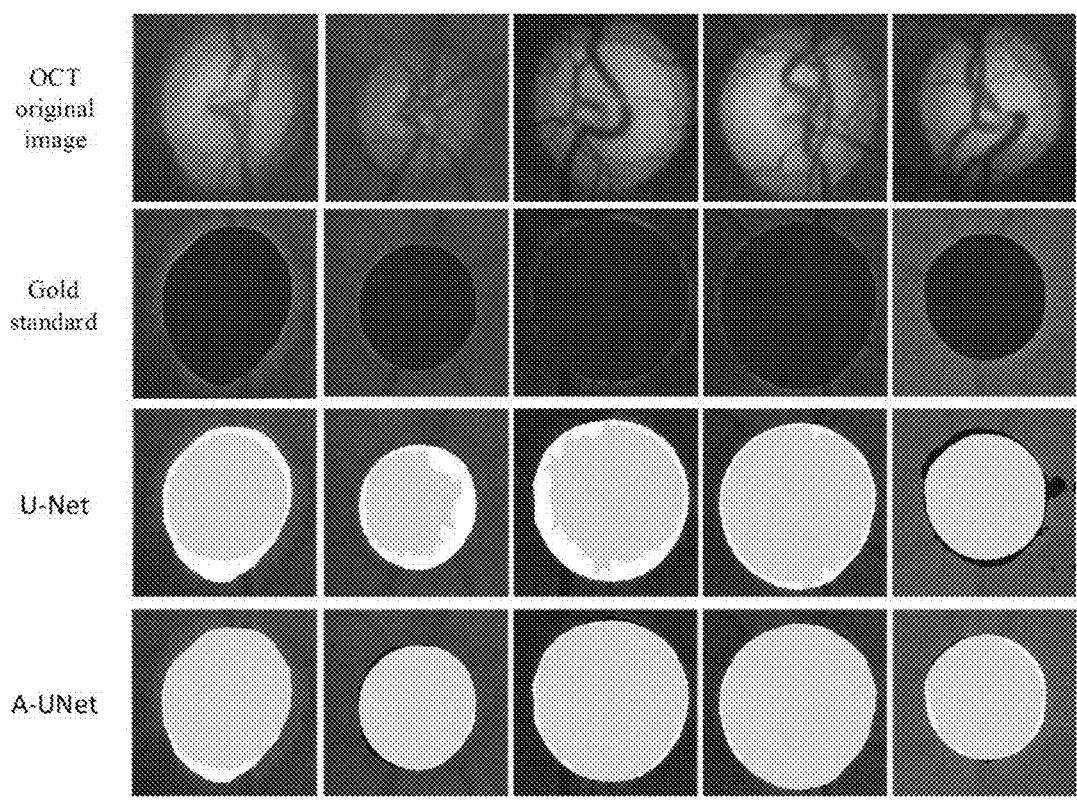
FIG. 6 is a visual comparison diagram of optic disc segmentation performances of U-Net and A-UNet on a glaucoma fundus color test diagram in a preferred embodiment of the present invention.

Specifically, Table 5 shows the comparison of optic disc segmentation performances of U-Net and A-UNet on the glaucoma fundus color test diagram; and FIG. 6 shows the visual comparison of optic disc segmentation performances of U-Net and A-UNet on the glaucoma fundus color test diagram.

TABLE 5

| Unit: pixel points |  | Test diagram 1 | Test diagram 2 | Test diagram 3 | Test diagram 4 | Test diagram 5 |
|---|---|---|---|---|---|---|
| Gold standard |  | 116812 | 87803 | 152543 | 153826 | 104499 |
| U-Net | Missing segmentation | 27049 | 31114 | 41418 | 15511 | 1009 |
|  | Segmentation result | 89763 | 56689 | 111125 | 138315 | 103490 |
|  | Over-segmentation | 0 | 0 | 0 | 0 | 5758 |
| A-UNet | Missing segmentation | 8883 | 1409 | 6947 | 3094 | 3 |
|  | Segmentation result | 107929 | 86394 | 145596 | 150732 | 62446 |
|  | Over-segmentation | 819 | 3749 | 443 | 1010 | 12037 |

Specifically, Table 6 is the comparison of segmentation performances of U-Net and A-UNet on a glaucoma fundus color image data test set.

TABLE 6

| Model | Optic cup | | | Optic disc | | |
|---|---|---|---|---|---|---|
|  | Dice | Recall/% | Accuracy/% | Dice | Recall/% | Accuracy/% |
| U-Net | 0.516 | 56.2 | 51.7 | 0.727 | 67.5 | 74.6 |
| A-UNet | 0.784 | 76.9 | 87.8 | 0.856 | 85.6 | 90.3 |

Specifically, in conjunction with the comparison of the data in Tables 2, 3, 4, 5 and 6, the segmentation performance of A-UNet is significantly better that of U-Net, indicating that the ophthalmic medical image segmentation method provided in the embodiment of the present application is superior to the existing ophthalmic medical image segmentation methods, shows favorable segmentation performances in different modal images and different lesion regions, and has strong robustness.

Embodiment 2

Figure 7:
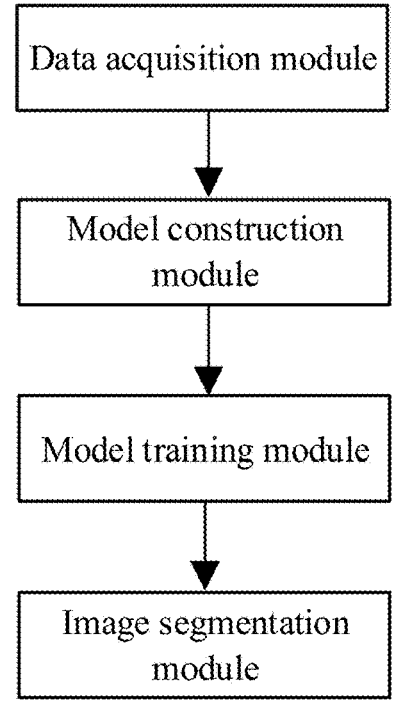
FIG. 7 is a module diagram of an ophthalmic medical image segmentation system in an embodiment of the present invention.

The present embodiment provides an ophthalmic medical image segmentation system. As shown in FIG. 7, the system includes:

a data acquisition module, configured to acquire medical image data of an ophthalmic lesion region, and divide the medical image data into a training set and a test set according to an autonomously set proportion;

a model construction module, configured to construct a weighted loss function by using a multi-loss fusion manner and construct a convolutional neural network model adopting a U-shaped encoding and decoding structure based on an attention mechanism and the weighted loss function;

a model training module, configured to perform training on the convolutional neural network model based on the training set and the test set; and an image segmentation module, configured to transmit a to-be-segmented medical image to the trained convolutional neural network model to obtain a segmentation result, wherein the U-shaped encoding and decoding structure includes an encoder, a bottleneck layer, a decoder and a jump connection part; the bottleneck layer is located between the encoder and the decoder; the attention mechanism is introduced into the decoder and the jump connection part;

a superficial layer feature map $I_{LE}$ of the encoder is subjected to a convolution operation to obtain $I_{LE-1}$, and a deep layer feature map $I_{HD}$ of the decoder is subjected to an up-sampling operation and the convolution operation to obtain $I_{HD-1}$; the $I_{LE-1}$ and the $I_{HD-1}$ are multiplied to obtain $I_{Mul}$; the $I_{Mul}$ and the $I_{HD-1}$ are summed, and $I_{Sum}$ is then output through an activation function; and the $I_{Mul}$ and the $I_{Sum}$ are spliced, and then output to a target layer.

The introduction to the ophthalmic medical image segmentation system provided by the present embodiment may refer to Embodiment 1, and will not be repeated here.

The present embodiment provides an ophthalmic medical image segmentation system with the same beneficial effect as the above-mentioned ophthalmic medical image segmentation method.

Embodiment 3

The present embodiment provides a computer-readable storage medium having stored a computer program therein, the computer program, when executed by a processor, implementing the steps of the ophthalmic medical image segmentation method described in Embodiment 1.

The introduction to the computer-readable storage medium provided by the present embodiment may refer to Embodiment 1, and will not be repeated here.

The computer-readable storage medium provided by the present embodiment has the same beneficial effect as the above-mentioned ophthalmic medical image segmentation method.

It should be understood by a person skilled in the art that the embodiments of the present application may be provided as methods, systems or computer program products. Therefore, the present application may adopt embodiments in forms of hardware only, software only, or a combination of software and hardware. Furthermore, the present application may adopt forms of computer program products executed on one or more computer usable storage media (including but not being limited to disk storage, CD-ROM and optical storage, etc.) containing computer usable program codes.

The present application is described with reference to the flowcharts and/or block diagrams of a method, a device (system) and a computer program product according to the embodiments of the present application. It should be understood that each process and/or block in the flowcharts and/or block diagrams, and combinations of processes and/or blocks in the flowcharts and/or block diagrams, may be realized by computer program instructions. These computer program instructions may be provided to a generate-purpose computer, a special-purpose computer, an embedded processor, or processors of other programmable data processing devices, to create a machine, such that an apparatus for realizing functions designated in one or more processes in the flowcharts and/or in one or more blocks in the block diagrams, may be created by instructions performed by a computer or processors of other programmable data processing devices.

These computer program instructions may further be stored in a computer readable storage that can guide a computer or other programmable data processing devices to work in a specific way, such that a manufactured product including an instruction apparatus may be created by the instructions stored in this computer readable storage, and this instruction apparatus realizes the functions designated in one or more processes in the flowcharts and/or in one or more blocks in the block diagrams.

These computer program instructions may further be loaded into a computer or other programmable data processing devices, such that a series of operating steps may be performed on the computer or other programmable data processing devices, so as to generate processes realized by the computer, such that steps for realizing the functions designated in one or more processes in the flowcharts and/or in one or more blocks in the block diagrams may be provided by the instructions executed on the computer or other programmable data processing devices.

Obviously, the above embodiments are only examples given to clearly illustrate the present application, without any limitation of implementations. For a person of ordinary skill in the art, other different forms of changes or variations can be made on the basis of the above description. There is no need and cannot be exhaustive of all implementations. The apparent changes or variations derived therefrom are still within the protection scope of the present invention.

The invention claimed is:

1. An ophthalmic medical image segmentation method, comprising the following steps:

acquiring medical image data of an ophthalmic lesion region, and dividing the medical image data into a training set and a test set according to an autonomously set proportion;

constructing a convolutional neural network model adopting a U-shaped encoding and decoding structure based on an attention mechanism and a weighted loss function;

performing training on the convolutional neural network model based on the training set and the test set; and transmitting a to-be-segmented medical image to the trained convolutional neural network model to obtain a segmentation result, wherein the U-shaped encoding and decoding structure includes an encoder, a jump connection part, a bottleneck layer and a decoder; the bottleneck layer is located between the encoder and the decoder; the encoder is connected to the decoder through the jump connection part; and wherein the attention mechanism introduced into the U-shaped encoding and decoding structure comprises the steps of:

subjecting a superficial layer feature map $I_{LE}$ of the encoder to a convolution operation to obtain a first processed feature map $I_{LE-1}$, and subjecting a deep layer feature map $I_{HD}$ of the decoder to an up-sampling operation and the convolution operation to obtain a second processed feature map $I_{HD-1}$;

multiplying the first processed feature map $I_{LE-1}$ and the second processed feature map $I_{HD-1}$ to obtain a multiplied feature map $I_{Mul}$;

summing the multiplied feature map $I_{Mul}$ and the second processed feature map $I_{HD-1}$, and outputting a result through an activation function to obtain a summed feature map $I_{Sum}$; and splicing the multiplied feature map $I_{Mul}$ and the summed feature map $I_{Sum}$, and then outputting to a target layer.

2. The ophthalmic medical image segmentation method according to claim 1, wherein the weighted loss function is constructed using a multi-loss fusion method, which is as follows:

a multi-classified logistic loss function, a Dice loss function and a binary cross entropy loss function are fused to obtain the weighted loss function $$\mathrm{Loss}_{All} : \mathrm{Loss}_{All} = \lambda_1 L_{logistic}(Y, \hat{Y}) + \lambda_2 L_{Dice}(Y, \hat{Y}) + \lambda_3 L_{BCE}(Y, \hat{Y});$$

wherein $\lambda_1$ is a weight of the multi-classified logistic loss function; $L_{logistic}(Y,\hat{Y})$ represents the multi-classified logistic loss function; $\lambda_2$ represents a weight of the Dice loss function; $L_{Dice}(Y,\hat{Y})$ represents the Dice loss function; $\lambda_3$ represents a weight of the binary cross entropy loss function; $L_{BCE}(Y,\hat{Y})$ represents the binary cross entropy loss function; $\lambda_1,\lambda_2,\lambda_3$ are all real numbers, and $\lambda_1+\lambda_2+\lambda_3=1$; and initial values of $\lambda_1,\lambda_2,\lambda_3$ are 0.4, 0.4, and 0.2 respectively.

3. The ophthalmic medical image segmentation method according to claim 2, wherein the multi-classified logistic loss function $L_{logistic}(Y,\hat{Y})$ is as follows:

$$L_{logistic}(Y, \hat{Y}) = -\sum_{\substack{x_i \in \Omega \\ i=1}}^{N} \omega_{logloss}(x_i) \cdot Y(x_i) \cdot \log[\hat{Y}(x_i)];$$

$$\omega_{logloss}(x_i) = \begin{cases} 10, & x_i \in ROI \\ 1, & x_i \in \mathrm{BACKGROUND} \end{cases};$$

wherein N is the number of pixel points, $x_i$ represents the $i^{th}$ pixel point, $\Omega$ represents a category of classification, $\Sigma$ is a summing symbol, $Y(x_i)$ represents a network segmentation result of the $i^{th}$ pixel point $x_i$, log represents that a logarithm is taken, $\hat{Y}(x_i)$ represents an expected segmentation result of the $i^{th}$ pixel point $x_i$, ROI represents a lesion region of interest, and BACKGROUND represents a background region;
the Dice loss function $L_{Dice}(Y,\hat{Y})$ is as follows:

$$L_{Dice}(Y, \hat{Y}) = 1 - \frac{2 \cdot [Y(x_i) \odot \hat{Y}(x_i)]}{\sum_{i=1}^{N}|Y(x_i)| + \sum_{i=1}^{N}|\hat{Y}(x_i)|};$$

wherein $\odot$ represents that the corresponding pixels are multiplied, and $\|$ represents that an absolute value is taken; and
the binary cross entropy loss function $L_{BCE}(Y,\hat{Y})$ is as follows:

$$L_{BCE}(Y, \hat{Y}) = -\frac{1}{N}\sum_{i=1}^{N}\{Y(x_i)\log[\hat{Y}(x_i)]\} + [1 - Y(x_i)] \cdot \log[1 - \hat{Y}(x_i)].$$

4. The ophthalmic medical image segmentation method according to claim 1, wherein the encoder is configured with a plurality of layers, and each layer is subjected to the convolution operation, a batch normalization operation and a maximum pooling operation; and the size of a convolution kernel and the number of operations for each layer to perform the convolution operation can be set autonomously.

5. The ophthalmic medical image segmentation method according to claim 4, wherein the encoder is configured with four layers, each layer is subjected to the convolution operation twice based on a convolution layer having a convolution kernel size of 3*3 and a step size of 1, and each layer is subjected to the maximum pooling operation based on a pooling layer having a pooling kernel size of 2*2.

6. The ophthalmic medical image segmentation method according to claim 1, wherein the medical image data comprises OCT image data of ophthalmic choroidal neo-vascularization and fundus color image data of glaucoma, and the OCT image data and the fundus color image data both contain original image data and corresponding gold standard image data.

7. The ophthalmic medical image segmentation method according to claim 6, wherein background pixel values in the OCT image data and the fundus color image data are assigned to 0, and the same pixel values are assigned to the lesion regions of the respective categories in the corresponding gold standard image data and incremented sequentially according to their categories.

8. A non-transitory computer-readable storage medium, having stored a computer program therein, the computer program, when executed by a processor, implementing the steps of the ophthalmic medical image segmentation method according to claim 1.

9. A non-transitory computer-readable storage medium, having stored a computer program therein, the computer program, when executed by a processor, implementing the steps of the ophthalmic medical image segmentation method according to claim 2.

10. A non-transitory computer-readable storage medium, having stored a computer program therein, the computer program, when executed by a processor, implementing the steps of the ophthalmic medical image segmentation method according to claim 3.

11. A non-transitory computer-readable storage medium, having stored a computer program therein, the computer program, when executed by a processor, implementing the steps of the ophthalmic medical image segmentation method according to claim 4.

12. A non-transitory computer-readable storage medium, having stored a computer program therein, the computer program, when executed by a processor, implementing the steps of the ophthalmic medical image segmentation method according to claim 5.

13. A non-transitory computer-readable storage medium, having stored a computer program therein, the computer program, when executed by a processor, implementing the steps of the ophthalmic medical image segmentation method according to claim 6.

14. A non-transitory computer-readable storage medium, having stored a computer program therein, the computer program, when executed by a processor, implementing the steps of the ophthalmic medical image segmentation method according to claim 7.

15. An ophthalmic medical image segmentation system, comprising:
a data acquisition module, configured to acquire medical image data of an ophthalmic lesion region, and divide the medical image data into a training set and a test set according to an autonomously set proportion;
a model construction module, configured to construct a weighted loss function by using a multi-loss fusion manner and construct a convolutional neural network model adopting a U-shaped encoding and decoding structure based on an attention mechanism and the weighted loss function;
a model training module, configured to perform training on the convolutional neural network model based on the training set and the test set; and
an image segmentation module, configured to transmit a to-be-segmented medical image to the trained convolutional neural network model to obtain a segmentation result, wherein the U-shaped encoding and decoding structure includes an encoder, a bottleneck layer, a decoder and a jump connection part; the bottleneck layer is located between the encoder and the decoder; the attention mechanism is introduced into the decoder and the jump connection part, said attention mechanism configured to:

subject a superficial layer feature map $I_{LE}$ of the encoder to a convolution operation to obtain a first processed feature map $I_{LE\text{-}1}$, and subject a deep layer feature map $I_{HD}$ of the decoder to an up-sampling operation and the convolution operation to obtain a second processed feature map $I_{HD\text{-}1}$;

multiply the first processed feature map $I_{LE\text{-}1}$ and the second processed feature map $I_{HD\text{-}1}$ to obtain a multiplied feature map $I_{Mul}$;

sum the multiplied feature map $I_{Mul}$ and the second processed feature map $I_{HD\text{-}1}$, and output a result through an activation function to obtain a summed feature map $I_{Sum}$; and splice the multiplied feature map $I_{Mul}$ and the summed feature map $I_{Sum}$, and then output to a target layer.

\* \* \* \* \*